U S 0 0 5 1 4 7 4 0 4 A

United States Patent [19]

Downey

[11] Patent Number: 5,147,404
[45] Date of Patent: Sep. 15, 1992

[54] VERTEBRA PROSTHESIS

[76] Inventor: Ernest L. Downey, 10559 S. Avenue G, Chicago, Ill. 60617

[21] Appl. No.: 607,367

[22] Filed: Oct. 24, 1990

Related U.S. Application Data

[60] Continuation-in-part of Ser. No. 522,076, May 10, 1990, Pat. No. 5,035,716, which is a continuation of Ser. No. 361,363, Jun. 5, 1989, abandoned, which is a division of Ser. No. 129,302, Dec. 7, 1987, Pat. No. 4,874,389.

[51] Int. Cl.⁵ .............................................. A61F 2/44
[52] U.S. Cl. ................................................... 623/17
[58] Field of Search .......................................... 623/17

[56] References Cited

U.S. PATENT DOCUMENTS

| 3,366,975 | 2/1968 | Pangman | 623/8 |
|---|---|---|---|
| 3,426,364 | 2/1969 | Lumb | 623/17 |
| 3,593,342 | 7/1971 | Niebauer | 623/16 |
| 3,867,728 | 2/1975 | Stubstad et al. | 623/16 |
| 4,229,839 | 10/1980 | Schwemmer | 623/16 |
| 4,599,086 | 7/1986 | Doty | 623/17 |
| 4,634,445 | 1/1987 | Helal | 623/21 |
| 4,636,217 | 1/1987 | Ogilvie et al. | 623/17 |
| 4,648,880 | 3/1987 | Brauman | 623/8 |
| 4,657,550 | 4/1987 | Daher | 623/17 |
| 4,820,305 | 4/1989 | Harms et al. | 623/16 |
| 4,863,477 | 9/1989 | Monson | 623/17 |
| 4,874,389 | 10/1989 | Downey | 623/17 |
| 4,926,849 | 5/1990 | Downey | 128/75 |

FOREIGN PATENT DOCUMENTS

| 2263842 | 7/1974 | Fed. Rep. of Germany . |
|---|---|---|
| 3023353A1 | 4/1981 | Fed. Rep. of Germany . |
| 3535112A1 | 4/1987 | Fed. Rep. of Germany . |
| 895433 | 4/1980 | U.S.S.R. . |

Primary Examiner—David Isabella
Assistant Examiner—Debra S. Brittingham
Attorney, Agent, or Firm—Frank J. Uxa

[57] ABSTRACT

An apparatus useful to replace at least a portion of a vertebra in a spinal column associated with a spinal cord which comprises a plurality of elements sized and adapted to be fitted together in a position to substantially surround the spinal cord and to act as at least a portion of the naturally occurring vertebra located in the position an assembly acting to secure the fitted together elements in place in the spinal column.

19 Claims, 1 Drawing Sheet

VERTEBRA PROSTHESIS

RELATED APPLICATIONS

This is a continuation-in-part of U.S. patent application Ser. No. 522,076 filed May 10, 1990, now U.S. Pat. No. 5,035,716, issued Feb. 25, 1992 which is a continuation of U.S. patent application Ser. No. 361,363 filed Jun. 5, 1989, now abandoned, which is a division of U.S. patent application Ser. No. 129,302, filed Dec. 7, 1987, now U.S. Pat. No. 4,874,389.

BACKGROUND OF THE INVENTION

The present invention relates to a medical prosthesis for the replacement of at least a portion of a naturally occurring vertebra. More particularly, the invention relates to a prosthesis for the replacement of an injured, diseased or otherwise malfunctioning vertebra which prosthesis has the ability of functioning, at least in part, as a naturally occurring vertebra.

One of human kind's major medical problems involves various difficulties with the back. In particular, back concerns may involve one or more vertebrae which are cushioned by discs positioned between the individual vertebrae. The vertebrae together function as a main component of the back bone, and together with the discs and spinal cord form the spinal column. Another important function of the vertebrae is to protect the spinal cord from injury. Individual vertebrae each include a hole through which the spinal cord passes.

Because of exertion, injury, illness, accident or abuse, one or more of the vertebrae and/or one or more discs may become damaged and/or not function properly. Minor problems of this type can be treated with medication and other non-invasive therapy. However, it is often necessary to remove at least a portion of the damaged and/or malfunctioning component or components of the spinal column. For example, when a disc becomes ruptured, the ruptured disc may be surgically removed and the two vertebrae from between which the disc is removed are fused together. This fusing results in a loss of flexibility since the two fused vertebrae are substantially inflexible relative to each other.

This problem with inflexibility is even more severe if a damaged vertebra is to be removed. For example, see Doty U.S. Pat. No. 4,599,086, and Ogilvie, et al U.S. Pat. No. 4,636,217. In each of these patented systems only a portion of the damaged vertebra is removed and replaced by an assembly which does not resemble the removed naturally occurring vertebra, and which is secured directly to the adjacent vertebrae on both sides of the damaged vertebra. Thus, using these systems there are three (3) vertebra spaces that are inflexible relative to each other.

Clearly it would be advantageous to provide a vertebra/disc replacement system which overcomes or at least reduces the severity of one or more of these problems, in particular the flexibility problems noted above.

SUMMARY OF THE INVENTION

A new apparatus useful to replace at least a portion of a vertebra in a spinal column associated with a spinal cord has been discovered. The present apparatus is structured to replace at least a portion, in particular substantially all, of a naturally occurring vertebra, e.g., which is damaged and/or is not functioning properly. The present system is structured so as to not substantially interfere with the spinal cord and/or to provide for substantial flexibility along the spinal column. In addition, the prosthetic apparatus of the present invention is relatively easy to install and is durable in use.

In one broad aspect, the present apparatus comprises a vertebra body including a plurality of elements, preferably two elements, sized and adapted to be fitted together to form an assembly in a position substantially surrounding the spinal cord and to act as at least a portion of a naturally occurring vertebra located in such position. Preferably the fitted together vertebra body acts as substantially the entire naturally occurring vertebra located in such position. A securement means is provided and acts to secure the fitted together vertebra body in place in the spinal column. The elements making up the vertebra body are fitted around the spinal cord rather than, as in certain prior art devices, away from the spinal cord. This feature allows more, and preferably substantially all, of a damaged naturally occurring vertebra to be replaced. The present vertebra body, in particular the plurality of elements, can be precision made, e.g., based on x-rays or other imaging techniques of the actual person or animal whose naturally occurring vertebra is to be at least partially replaced. Thus, although great care is needed to insure that the present system has substantially no detrimental effect on the spinal cord, such care is provided by custom or individually adapting a specific vertebra body to the individual being treated. In addition, the plurality of elements concept allows the spinal cord to be substantially completely surrounded substantially without interfering, or even touching, the cord itself.

In another broad aspect of the invention, an artificial vertebra element is provided which is sized and adapted to be placed in a position to act as at least a portion, preferably as substantially all, of the naturally occurring vertebra located in such position. A securement means is provided which acts to secure this vertebra element directly to at least one of a first disc prosthesis, e.g., located at or near a first end of the vertebra element, and a second disc prosthesis, e.g., located at or near a substantially opposing second end of the vertebra element. In this embodiment, the naturally occurring disc or discs which would normally be located adjacent the artificial vertebra element are at least partially, preferably substantially totally, removed and replaced by the above-noted disc prosthesis.

This "disc securement" feature of the present invention is very important in that a substantial degree of flexibility is retained since the artificial vertebra element is not fused (or otherwise secured) directly to the other vertebrae in the spinal column, as with certain of the prior art systems. Since relatively little, if any, flexibility is lost, the present system can be used to replace two or more of the vertebrae, if such is necessary and/or desirable. Such "multi-vertebrae" replacement is within the scope of the present invention.

Each of the features of the present system can be used in combination with any one or more of the other features of the present system, and all such combinations are within the scope of the present invention. For example, the "disc securement" feature can be used in combination with the "plurality of elements" feature.

The vertebra body or element is preferably customized to the individual being treated. In a particularly useful embodiment, the vertebra body or element has substantially the shape of a naturally occurring vertebra having pedicles, laminae and processes, especially substantially the shape of the naturally occurring vertebra being replaced by the vertebra body or element of the present invention.

With further regard to the "plurality of vertebra elements" embodiment, preferably such elements are structured so that only one fitted together configuration is possible. For example, the individual elements can be keyed, e.g., with projections and indents, so that the elements must be relatively positioned in one particular way to be properly fitted together. In particular, the plurality of elements may include at least two spaced apart projections and at least two spaced apart indents sized and adapted so that each of the projections is matingly engaged into one of the indents when the plurality of elements are fitted together. Having the plurality of elements fit together in only one configuration reduces the chances of surgical error when installing the present system and makes it relatively easy to precisely install the present system.

Another feature of the present system is the inclusion of a tissue securement means which acts to at least assist in securing or adhering bodily tissue to the present vertebra body or element following installation of the same. Such tissue securement means may include, for example, a quantity of conventional bonding composition and/or glue (adhesive) located on the surface of the vertebra body or element and/or one or more through holes in the vertebra body or element, e.g., to allow tissue (muscle and the like) to be sutured directly to the element or assembly. Any type of bonding composition or adhesive may be used provided it has sufficient bonding ability and has no substantial detrimental effect on the present system or on the individual being treated. Such bonding composition may be chosen from those which promote the growth and/or adhesion of tissue to a surface. Examples of such bonding compositions or adhesives include, but are not limited to, polymethylmethacrylate, fibrin glue, mussel adhesive protein and the like.

Such adhesive may also be used to bond or secure the plurality of elements together. Of course, other means, e.g., mechanical means such as wires, rods and the like, may be employed to secure the plurality of elements together.

The material or materials of construction used for the vertebra body or element should be such as to be able to endure the stresses and environment to which a vertebra prosthesis is subjected. In addition, such material of construction should be biocompatible, and substantially chemically inert so as not to cause any substantial detrimental effect to the individual in whom the vertebra prosthesis is implanted. Materials such as various metals and/or polymeric materials, which are conventionally used in bone prosthesis implants may be used.

In certain embodiments, the vertebra body or element is secured to one or two disc prosthesis. Such disc prosthesis may include outwardly extending securement means which act to secure the disc prosthesis to the vertebra body or element. Such a disc prosthesis is disclosed in Downey U.S. Pat. No. 4,874,389, which is incorporated in its entirety by reference herein. The disc prosthesis or replacement discs of the present invention may include a body portion which has an inner portion and an outer portion, or the body portion may be substantially uniform throughout.

The material or materials of construction of the body portion should be biocompatible and substantially chemically inert and insoluble in the environment in which the replacement disc is utilized. If the body portion is substantially uniform and/or made of a single material of construction, the body portion preferably comprises silicone elastomer, in particular silastic elastomer.

First and second securement means may extend out from the first and second substantially opposing surfaces, respectively, of the body portion and act to secure the replacement disc to the first and second adjacent vertebrae, respectively, at least one of which vertebrae is a vertebra prosthesis of the present invention. In one embodiment, each of the first and second securement means comprises a threaded member. In a particularly useful embodiment, the threaded member of the first securement means is threaded in the opposite direction relative to the threaded member of the second securement means. Such opposite direction threading allows the threaded members of both the first and second securement means to be threaded into both adjacent vertebrae simultaneously. This reduces the amount of manipulation required to properly set the replacement disc in place so that the body portion is fit and held between the adjacent vertebrae.

Preferably, each of the threaded members is tapered toward the end of the threaded member away from the body portion. The end of the threaded away from the body portion preferably includes a substantially flat end surface. The surface area of the end of the threaded member away from the body portion is in the range of about 30% to about 60% of the surface area of the threaded member at the surface of the body portion.

The first and second securement means may include a first base and a second base, respectively, each of which is located in the body portion. Such bases act to secure or anchor the securement means to the body portion. Although the first and second bases can be separate components, in one embodiment the first base and second base are parts of the same component. Such embodiment is particularly useful if it is desired to have a replacement disc of increased stiffness or reduced flexibility.

In one embodiment, the first base and the second base each extend in the body portion radially from the longitudinal axis of the first and second securement means, respectively. This radial extension feature more effectively anchors or secures the base means and securement means to the body portion.

Each of the securement means should be made of material or materials which are biocompatible and substantially inert and insoluble in the environment in which they are to be utilized. In one particularly useful embodiment, the securement means are made of metal, such as stainless steel.

The first and second securement means can be linked together, in particular by inter-engaging loop segments. Thus, for example, the bases of the first and second securement means can each terminate in a loop, which loops are linked together inside the body portion. Such inter-engaged loops provide added stability to the replacement disc and provide for increased coordination between the two adjacent vertebrae. This structure is more rigid because of the inter-engaging loop members. However, it is not as rigid as the structure in which both the first base and the second base are parts of the same component.

In instances when the vertebra body or element is secured to one or two replacement discs or disc prosthesis, it is preferred that the vertebra body or element include at least one securement indent, preferably two substantially opposing securement indents. These securement indents are sized and adapted to receive and hold the outwardly extending securement means, e.g., threaded securement members of the replacement discs described above. In a particularly useful embodiment, the vertebra body or element includes at least one, and preferably two, cups. Such cups are fitted into the securement indents of the vertebra body or element and are sized to receive the securement members of the disc prosthesis. Such cup or cups are preferably made of material different from the remainder of the vertebra body or element. More preferably, the cup or cups are made of a softer material than is the remainder of the vertebra body or element. This facilitates securing, e.g., threading, the disc prosthesis to the vertebra body or element without substantially detrimentally affecting the structural integrity of the vertebra body or element.

These and other aspects and advantages of the present invention are set forth in the following detailed description and claims, particularly when considered in conjunction with the accompanying drawings in which like parts become like reference numerals.

DETAILED DESCRIPTION OF THE DRAWINGS

Figure 1:
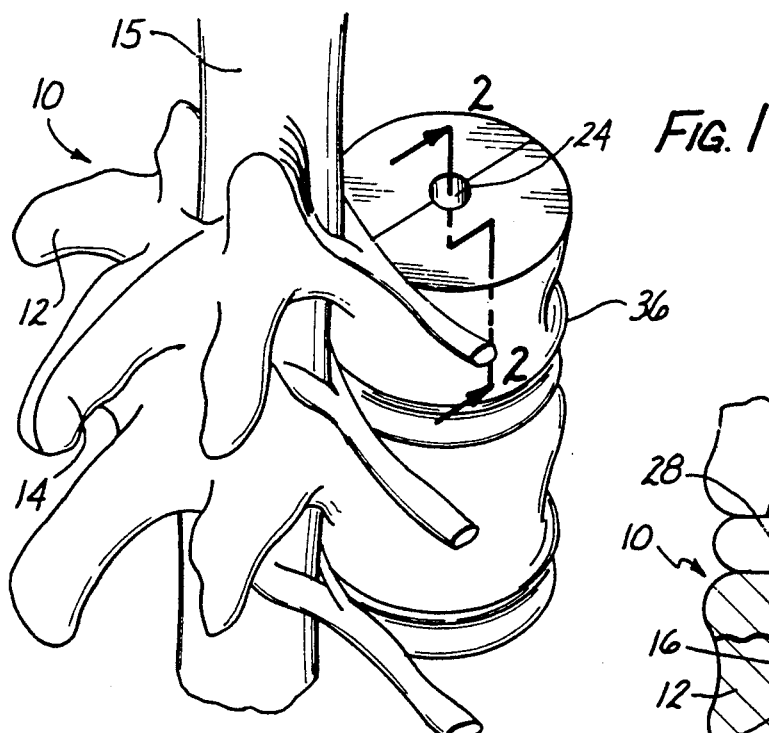
FIG. 1 is top-side view, in perspective showing one embodiment of the present vertebra prosthesis in use. For illustration clarity, the replacement disc 30 and second vertebra prosthesis directly above vertebra prosthesis 10 are not shown in FIG. 1.

Referring now to the drawings, a vertebra prosthesis, shown generally as 10, includes a first half portion 12 and a second half portion 14. As will be discussed in detail hereinafter, vertebra prosthesis 10 is formed by putting first and second half portions 12 and 14 together around spinal cord 15 in the appropriate place in the spinal column of a mammal, in particular a human being.

Both first and second half portions 10 and 12 may be made of any suitable material which can be molded or otherwise shaped or formed into the requisite configuration so that when fitted together first and second half portions look and function as a naturally occurring vertebra which is to be replaced by vertebra prosthesis 10. Alternately, first and second half portions may be configured so that together they look and function as a vertebra that is missing from the mammal's spinal column or as a normal vertebra replacing a malformed and/or malfunctioning vertebra.

Vertebra prosthesis 10 may be formed based on x-ray pictures and/or other sophisticated imaging techniques of the mammal's spinal column to ensure that the vertebra prosthesis is shaped precisely as desired. Each vertebra prosthesis 10 is preferably custom made to the exact requirements of the individual involved. For example, if more than one vertebra prosthesis is used in a single individual, each prosthesis is shaped somewhat differently, depending, for example, on where in the spinal column each vertebra prosthesis is placed. Also, different individuals may, and most probably will, require a differently sized/shaped vertebra prosthesis even if such prosthesis is to be placed at the same point in the spinal column. The present vertebra prosthesis is particularly adaptable to such customization.

Vertebra prosthesis 10, in particular first and second half portions 12 and 14, are constructed so as to fit together in only one way. This is a substantial advantage since the surgeon implanting vertebra prosthesis 10 has a positive indication that the prosthesis has been installed correctly. In vertebra prosthesis 10, this is achieved by a series of indents 16 in first half portion 12 and a corresponding number of projections 18 on second half portion 14. Indents 16 are located in first abutting surface 20, while projections 18 are located on second abutting surface 22. Each indent 16 is sized to receive a projection 18. The indents 16 and projections 18 are spaced apart in/on first and second abutting surfaces 20 and 22, respectively, so that when first and second abutting surfaces 20 and 22 are brought into abutting relation each indent 16 receives a projection 18. Thus, first and second half portions 12 and 14 are maneuvered until the first and second abutting surfaces are brought into abutting relation. This abutting relation is an indication that the two half portions 12 and 14 have been fitted together properly to form vertebra prosthesis 10.

First and second half portions 12 and 14 can be secured or bonded together using adhesives, bonding agents, wires, other mechanical and/or chemical means and the like.

First and second half portions 12 and 14 are shaped so that when first and second abutting surfaces 20 and 22 are secured together a first recess 24 and a second recess 26 are formed and, in addition, a channel 27 is provided through which the spinal cord 15 passes. First and second recesses 24 and 26 are sized to receive threaded members of replacement disc, such as threaded members 28 of replacement discs 30. At the same time vertebra prosthesis 10 is installed, it is preferred to install replacement discs 30 both above and below the vertebra prosthesis. In this manner vertebra prosthesis 10 is securely anchored in place.

In order to facilitate securing threaded members 28 of replacement disc 30 to vertebra prosthesis 10, the top and bottom recesses 24 and 26 are provided with liner cups 32 which are bonded in place using adhesives, bonding agents and the like. Liner cups 32 substantially conform to the shape of first and second recesses 24 and 26 and are made of a material which receives the threaded member 28 of artificial disc 30 more readily and/or easily than does the material from which first and second half portions 12 and 14 are made. For example, liner cups 32 may be made of a softer material, e.g., a softer polymeric material, relative to first and second half portions 12 and 14.

In any event liner cups 32 and threaded members 28 are relatively sized so that threaded member 28 can be threadally secured to liner cup 32. Adhesives and/or bonding agents may be used to more firmly secure threaded members 28 to vertebra prosthesis 10.

In order to provide for proper alignment of vertebra prosthesis 10 in the mammal's spinal column, it is often desirable to adhere certain tissue, e.g., muscle and the like, to the prosthesis. Eventually, tissue near the mammal's spinal column may grow to the vertebra prosthesis 10 and also assist in maintaining proper alignment.

Vertebra prosthesis 10 includes a plurality of relatively small through holes 34 which are suitable for initially securing (adhering) tissue to the vertebra prosthesis. Thus, during the surgical installation of vertebra prosthesis 10, tissue can be adhered to the prosthesis using sutures which pass through holes 34. In addition, or alternately, the outer surface 36 of vertebra prosthesis 10 can be coated, partially or completely, with a bonding agent, a growth promotor and the like to facilitate the adhesion and/or growth of tissue to the vertebra prosthesis 10.

Figure 2:
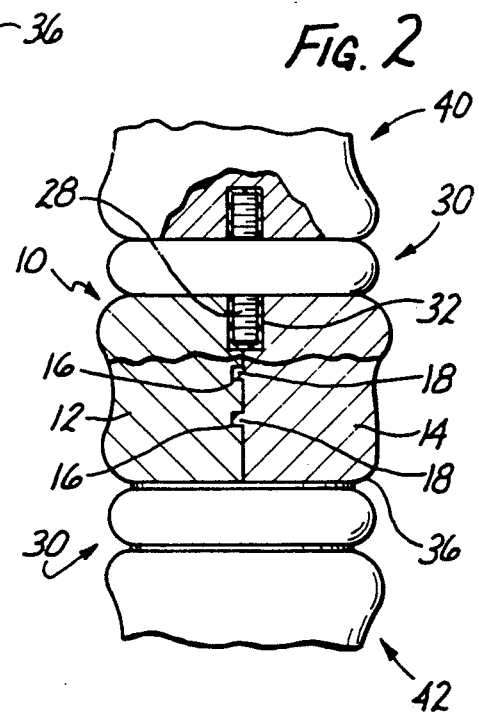
FIG. 2 is a cross-sectional view taken generally along line 2—2 FIG. 1.
Figure 3:
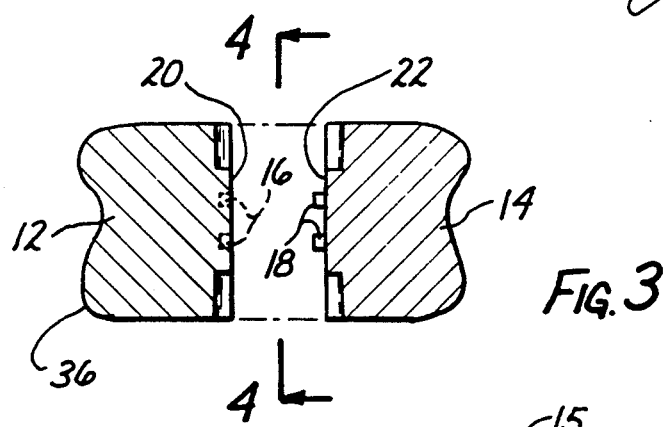
FIG. 3 is cross-sectional view showing the two halves of the vertebra prosthesis embodiment shown in FIGS. 1 and 2 separated.
Figure 4:
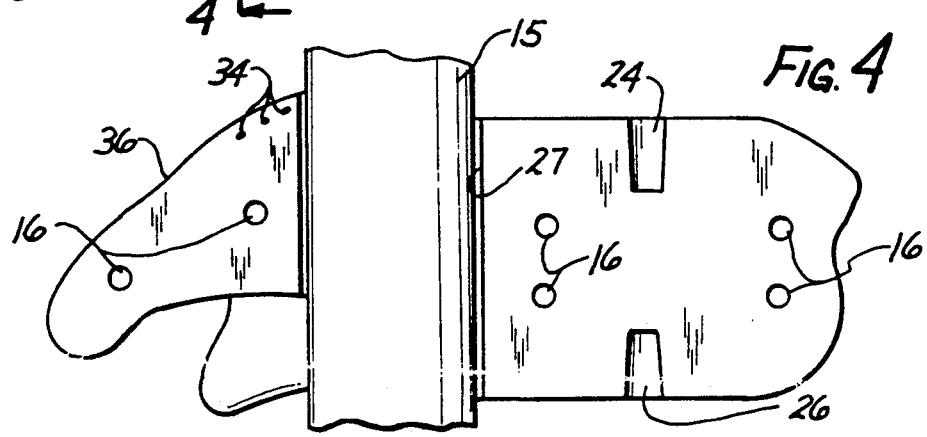
FIG. 4 is a cross-sectional view taken generally along line 4—4 of FIG. 3.

Note that in FIG. 2, a second vertebra prosthesis 40 is located above vertebra prosthesis 10 and is structured and functions in a manner substantially similar to vertebra prosthesis 10. Second vertebra prosthesis 40 has a slightly different size/shape than does vertebra prosthesis 10 because it is positioned at a different location in the mammal's spinal column. Second vertebra prosthesis 40 is secured to replacement disc 30 in substantially the same manner as vertebra prosthesis 10 is secured to replacement disc 30. The vertebra 42 located below vertebra prosthesis 10 is a naturally occurring vertebra. A threaded member 28 from replacement disc 30 is threaded directly into vertebra 42 to secure replacement disc 30 to vertebra 42.

The vertebra prosthesis 10 may be installed as follows. Once it is determined that a vertebra is to be replaced, detailed measurements, e.g., using X-rays and/or other imaging techniques, are made so that vertebra prosthesis 10 can be made which has substantially the same configuration as the vertebra to be replaced had when healthy. Surgery is then performed in which the vertebra to be replaced as well as the discs on either side of this vertebra, are removed. This can be accomplished by separating the vertebrae in question using an apparatus as disclosed in Downey U.S. Pat. No. 4,926,849, which is incorporated in its entirety by reference herein. The separation can occur sequentially so that the vertebra to be replaced is separated from each of the two adjacent vertebrae one at a time, or the three vertebrae can be separated simultaneously. In any event, once the vertebrae are separated, the disc between the vertebrae is removed and replaced by a replacement disc 30. This replacement disc 30 is secured to the vertebra that is to remain, but not to the vertebra that is to be replaced.

After both discs associated with the vertebrae to be replaced are removed, e.g., using conventional techniques, the vertebrae on either side of this vertebra are separated to provide more than normal separation of these vertebrae and to give the surgeon some working room. After this separation, the vertebra to be replaced is carefully removed, e.g., using conventional techniques. The vertebra prosthesis 10 is inserted around the spinal cord. The separating force on the vertebrae on either side of the vertebra prosthesis 10 is released. The vertebra prosthesis 10 is secured to both replacement discs and other work, as necessary, is performed to secure the vertebra prosthesis in place and to secure other of the patient's tissue to the vertebra prosthesis. The surgical procedure is then concluded.

One important feature of the present invention is that more than one vertebra can be replaced using a plurality of different vertebra prosthesis, such as vertebra prosthesis 10 and second vertebra prosthesis 40. In fact, the majority or even all of the vertebrae of a single mammal can be replaced using the system of the present invention.

The present vertebra prosthesis provides outstanding advantages. It is relatively easy to install and requires relatively little surgical technique. The entire vertebra is replaced rather than only a portion of the vertebra as in certain prior art systems. The coupling of the vertebra prosthesis to the other vertebrae is relatively simple and is done with little or no outward manifestation of such coupling. The vertebra prosthesis looks substantially like a naturally occurring vertebra so that little or no disfigurement results. More than one, or even all, of a mammal's vertebrae can be replaced using the present system. Thus, the present system is particularly applicable to instances where the spinal cord has been damaged or injured along a substantial portion of its length. The naturally occurring vertebrae can be removed, e.g., so as to facilitate repairing the spinal cord, and then replaced by a plurality of vertebra prosthesis according to the present invention.

While this invention has been described with respect to various specific examples and embodiments, it is to be understood that the invention is not limited thereto and that it can be variously practiced within the scope of the following claims.

What is claimed is:

1. An apparatus useful to replace at least a portion of a vertebra in a spinal column associated with a spinal cord which comprises:
   a vertebra body including a plurality of elements sized and adapted to be fitted together in a position to substantially surround the spinal cord, said vertebra body having the same shape as a naturally occurring vertebra having pedicles, laminae and processes which is located in said position and acting as at least a portion of a naturally occurring vertebra located in said position; and
   a securement assembly located in conjunction with said vertebra body and adapted to secure said vertebra body in place in the spinal column.

2. The apparatus of claim 1 wherein said securement assembly is adapted to secure said vertebra body directly to a first disc prosthesis and to a second disc prosthesis.

3. The apparatus of claim 1 wherein said vertebra body is customized to meet the requirements of the specific application in which it is to be used.

4. The apparatus of claim 1 wherein said plurality of elements are structured so that said plurality of elements can be fitted together in only one configuration.

5. The apparatus of claim 4 wherein said plurality of elements include at least two projections and at least two indents sized and adapted so that each of said projections is matingly engaged into one of said indents when said plurality of elements are fitted together.

6. The apparatus of claim 1 wherein said vertebra body further includes tissue securement means acting to at least assist in securing or adhering bodily tissue to said vertebra body when said vertebra body is in said position.

7. The apparatus of claim 3 wherein said vertebra body is customized based at least in part on one or more images of the spinal column of the patient in whose body said vertebra body is to be placed.

8. The apparatus of claim 1 wherein the vertebra body elements together are adapted to replace substantially an entire naturally occurring vertebra located in said position.

9. An apparatus useful to replace at least a portion of a vertebra in a spinal column associated with a spinal cord which comprises:

an artificial vertebra element sized and adapted to be placed in a position to act as at least a portion of the naturally occurring vertebra located in said position; and a securement assembly located in conjunction with said vertebra element and adapted to facilitate securing said vertebra element directly to at least one of a first disc prosthesis and a second disc prosthesis, said securement assembly including substantially opposing first and second securement indents located in said vertebra element and being sized and adapted to receive and hold first and second outwardly extending securement members included in the first disc prosthesis and the second disc prosthesis, respectively.

10. The apparatus of claim 9 wherein said vertebra element has substantially the same shape as the naturally occurring vertebra having pedicles, laminae and processes which is located in said position.

11. The apparatus of claim 9 wherein said vertebra element further includes securement means acting to at least assist in securing or adhering bodily tissue to said vertebra element when said vertebra element is in said position.

12. The apparatus of claim 9 wherein said first and second securement indents include a first cup and a second cup, respectively, said first and second cups each being fitted into said first and second securement indents, respectively, and being sized to receive said first and second securement members, respectively.

13. The apparatus of claim 9 wherein said securement assembly is adapted to facilitate securing said vertebra element directly to a first disc prosthesis and a second disc prosthesis.

14. The apparatus of claim 9 wherein said vertebra element is adapted to replace substantially the entire naturally occurring vertebra located in said position.

15. An apparatus useful to replace at least a portion of a vertebra and substantially all of both discs directly associated with the naturally occurring vertebra to be replaced which comprises:

a first disc prosthesis adapted to be secured to the first vertebra adjacent the vertebra to be replaced, said first disc prosthesis being sized and adapted to replace and act as substantially all of the first naturally occurring disc located between said first vertebra and said vertebra to be replaced;

an artificial vertebra element sized and adapted to be placed in a position to act as at least a portion of said vertebra to be replaced;

a second disc prosthesis adapted to be secured to the second vertebra adjacent the vertebra to be replaced, said second disc prosthesis being sized and adapted to replace and act as substantially all of the second naturally occurring disc located between said second vertebra and said vertebra to be replaced; and a securement assembly located in conjunction with said vertebra element and adapted to secure said vertebra element directly to said first disc prosthesis and said second disc prosthesis.

16. The apparatus of claim 15 wherein said vertebra element is adapted to replace substantially the entire vertebra to be replaced and has substantially the same shape as the vertebra to be replaced.

17. The apparatus of claim 16 wherein said vertebra element is derived from a plurality of elements sized and adapted to be fitted together to substantially surround the spinal cord and form said vertebra element.

18. The apparatus of claim 17 wherein said plurality of elements are structured so that said plurality of elements can be fitted together in only one configuration.

19. The apparatus of claim 18 wherein said plurality of elements include at least two projections which are integral with said plurality of elements and at least two indents sized and adapted so that each of said projections is matingly engaged into one of said indents when said plurality of elements is fitted together.

* * * * *